(12) United States Patent
Kantrowitz et al.

(10) Patent No.: US 7,513,864 B2
(45) Date of Patent: Apr. 7, 2009

(54) SYNCHRONIZATION SYSTEM BETWEEN AORTIC VALVE AND CARDIAC ASSIST DEVICE

(76) Inventors: Allen B. Kantrowitz, 190 Torrey Woods Rd., Williamstown, MA (US) 01267; Adrian Kantrowitz, 70 Gallogly Rd., Auburn Hills, MI (US) 48326

( * ) Notice: Subject to any disclaimer, the term of this patent is extended or adjusted under 35 U.S.C. 154(b) by 207 days.

(21) Appl. No.: 11/178,969

(22) Filed: Jul. 11, 2005

(65) Prior Publication Data

US 2006/0030747 A1    Feb. 9, 2006

Related U.S. Application Data

(60) Provisional application No. 60/586,537, filed on Jul. 9, 2004.

(51) Int. Cl.
*A61M 1/12* (2006.01)
(52) U.S. Cl. .................. 600/18; 600/16; 600/17; 604/914
(58) Field of Classification Search ............ 600/16–18, 600/514, 527, 528; 604/914; 623/3.1, 3.26, 623/3.28
See application file for complete search history.

(56) References Cited

U.S. PATENT DOCUMENTS

| 4,077,394 | A |   | 3/1978  | McCurdy ................. 128/1 D |
| 4,630,597 | A | * | 12/1986 | Kantrowitz et al. ........... 600/18 |
| 4,692,148 | A | * | 9/1987  | Kantrowitz et al. ......... 600/509 |
| 4,809,681 | A | * | 3/1989  | Kantrowitz et al. ........... 600/17 |
| 4,902,272 | A | * | 2/1990  | Milder et al. ................. 600/18 |
| 5,188,106 | A | * | 2/1993  | Nappholz et al. ............. 607/24 |
| 5,456,665 | A | * | 10/1995 | Postell et al. ........... 604/103.09 |
| 5,913,814 | A | * | 6/1999  | Zantos ........................ 600/18 |

(Continued)

OTHER PUBLICATIONS

Lee et al. "Skeletal muscle extraaortic counterpulsation. A true arterial counterpulsation." J Thorac Cardiovasc Surg, Nov. 1991; 102(5):757-65.

(Continued)

*Primary Examiner*—Carl H Layno
*Assistant Examiner*—Yun Haeng Lee
(74) *Attorney, Agent, or Firm*—Gifford, Krass, Sprinkle, Anderson & Citkowski, P.C.

(57) ABSTRACT

A cardiac assist device synchronization system includes a cardiac assist device and an acoustic or accelerometer sensor that provides a signal input to the cardiac assist device indicative of aortic valve closure. The cardiac assist device is coupled to a mammalian aorta and includes an inflatable chamber and a fluid pump. A fluid conduit is in communication between the chamber and the pump to provide for selective inflation of the chamber. A pump controller triggers the pump in counter-pulsation to a mammalian heart upstream from the aorta. A process for synchronizing a cardiac assist device in counter-pulsation with a left ventricle includes locating an acoustic or accelerometer sensor within a thoracic cavity of a mammal having the assist device coupled to the aorta of the mammal. Through the measurement of an acoustic or acceleration property of an aortic valve of the mammal, and the transmission of aortic valve closure measurement through a controller for the cardiac assist device, counter-pulsatile synchronization for the cardiac assist device is achieved.

12 Claims, 1 Drawing Sheet

U.S. PATENT DOCUMENTS

| | | | |
|---|---|---|---|
| 6,132,363 A * | 10/2000 | Freed et al. | 600/16 |
| 6,251,061 B1 | 6/2001 | Hastings et al. | 600/16 |
| 6,398,738 B1 * | 6/2002 | Millar | 600/486 |
| 6,589,267 B1 | 7/2003 | Hui | 606/202 |
| 6,623,420 B2 | 9/2003 | Reich et al. | 600/17 |
| 6,679,829 B2 * | 1/2004 | Nigroni et al. | 600/18 |
| 2003/0125601 A1 * | 7/2003 | Schock et al. | 600/18 |
| 2003/0191357 A1 * | 10/2003 | Frazier | 600/16 |
| 2003/0195428 A1 * | 10/2003 | Brockway et al. | 600/486 |
| 2004/0097783 A1 * | 5/2004 | Peters et al. | 600/16 |
| 2004/0152945 A1 * | 8/2004 | Kantrowitz et al. | 600/18 |

OTHER PUBLICATIONS

Chachques et al. "Dynamic aortomyoplasty to assist left ventricular failure." Ann Thorac Surg, Feb. 1990; 49(2):225-30.

Girsch et al. "Experimental development of an electrically stimulated biological skeletal muscle ventricle for chronic aortic counterpulsation." Eur J Cardiothorac Surg, Jan. 1998; 13(1):78-83.

Hayward "Dynamic cardiomyoplasty: time to wrap it up?" Heart, Sep. 1999; 82:263-264.

Salmons et al. "Cardiac assistance from skeletal muscle: a critical appraisal of the various approaches." British Heart Journal, 1992; 68:333-338.

\* cited by examiner

SYNCHRONIZATION SYSTEM BETWEEN AORTIC VALVE AND CARDIAC ASSIST DEVICE

RELATED APPLICATION

This application claims priority of U.S. Provisional Patent Application Ser. No. 60/586,537 filed Jul. 9, 2004, which is incorporated herein by reference.

FIELD OF THE INVENTION

The present invention in general relates to a cardiac assist device and more specifically to controlled pulsation of such an assist device in cooperation with a subject heart.

BACKGROUND OF THE INVENTION

A major cause of death and disability is the failure of the cardiac left ventricle to adequately perfuse the body with blood. While numerous disease conditions cause left ventricular failure, coronary artery disease is perhaps the most common. Regardless of the cause, ineffectual ejection from the left ventricle further weakens the heart since the heart receives blood supply through coronary arteries during the resting phase. As the heart muscle loses the ability to pump blood, both systolic and diastolic blood pressures are reduced with a reduced diastolic pressure. The pressure maintained in the arteries during the time of heart muscle relaxation is reduced thereby limiting blood flow through the coronary arteries. With reduced blood flow through the heart itself, the heart muscle is further deprived of essential nutrients.

The prior art includes numerous cardiac assist devices that work in concert with a failing heart in order to increase cardiac ejection volume and pressure. One form of cardiac assist device that has met with some success is the left ventricular assist device (LVAD) that is a secondary pump located in operative communication with the aorta in order to improve blood flow characteristics from an adjacent failing heart. A left ventricular assist device is known in the art to take the form of an intra-aortic balloon pump, a patch pump sutured to the aortic wall, and a cuff constrictive about the aorta. A common feature of all these variants of LVADs is a pulsatile pumping that is phase synchronized to coincide with the point of inflection associated with the end of the cardiac systolic phase and the beginning of diastole. This point of inflection is commonly referred to as the dicrotic notch. The timing of LVAD pumping in a counter-pulsatile fashion that commences at the dicrotic notch is critical in optimizing auxiliary pumping effectiveness. Physiologically, the dicrotic notch correlates with closure of the aortic valve.

The electrocardiogram (EKG) cannot accurately predict the timing of the dicrotic notch since the time delay in the EKG reading relative to aortic closure is unknown. Prior art attempts to measure the time delay in EKG for determining the dicrotic notch have included blood pressure monitoring. Representative blood pressure monitoring schemes are provided in U.S. Pat. Nos. 4,077,394 and 6,623,420. Unfortunately, implanted pressure sensors tend to foul over time while noninvasive pressure sensors tend to shift position and detract from patient quality of life.

As an alternative approach an implanted microphone has been contemplated in sensing aortic valve opening in the context of LVAD based on direct intrinsic compression of the ventricle, as exemplified in U.S. Pat. No. 6,251,061 B1. However, ferrofluid pumping to compress the heart remains an untested technology that is surgically intensive to implement.

Thus, there exists a need for a system to control counterpulsation in an LVAD with precise timing control relative to the closure of the aortic valve and independent of a pressure sensor.

SUMMARY OF THE INVENTION

A cardiac assist device synchronization system includes a cardiac assist device and an acoustic or accelerometer sensor that provides a signal input to the cardiac assist device indicative of aortic valve closure. The cardiac assist device is coupled to a mammalian aorta and includes an inflatable chamber and a fluid pump. A fluid conduit is in communication between the chamber and the pump to provide for selective inflation of the chamber. A pump controller triggers the pump in counter-pulsation to a mammalian heart upstream from the aorta.

A process for synchronizing a cardiac assist device in counter-pulsation with a left ventricle includes locating an acoustic or accelerometer sensor within a thoracic cavity of a mammal having the assist device coupled to the aorta of the mammal. Through the measurement of an acoustic or acceleration property of an aortic valve of the mammal, and the transmission of aortic valve closure measurement through a controller for the cardiac assist device, counter-pulsatile synchronization for the cardiac assist device is achieved.

BRIEF DESCRIPTION OF THE DRAWING

The present invention is further detailed with respect to the following exemplary, non-limiting drawing.

DETAILED DESCRIPTION OF THE INVENTION

Figure 1:
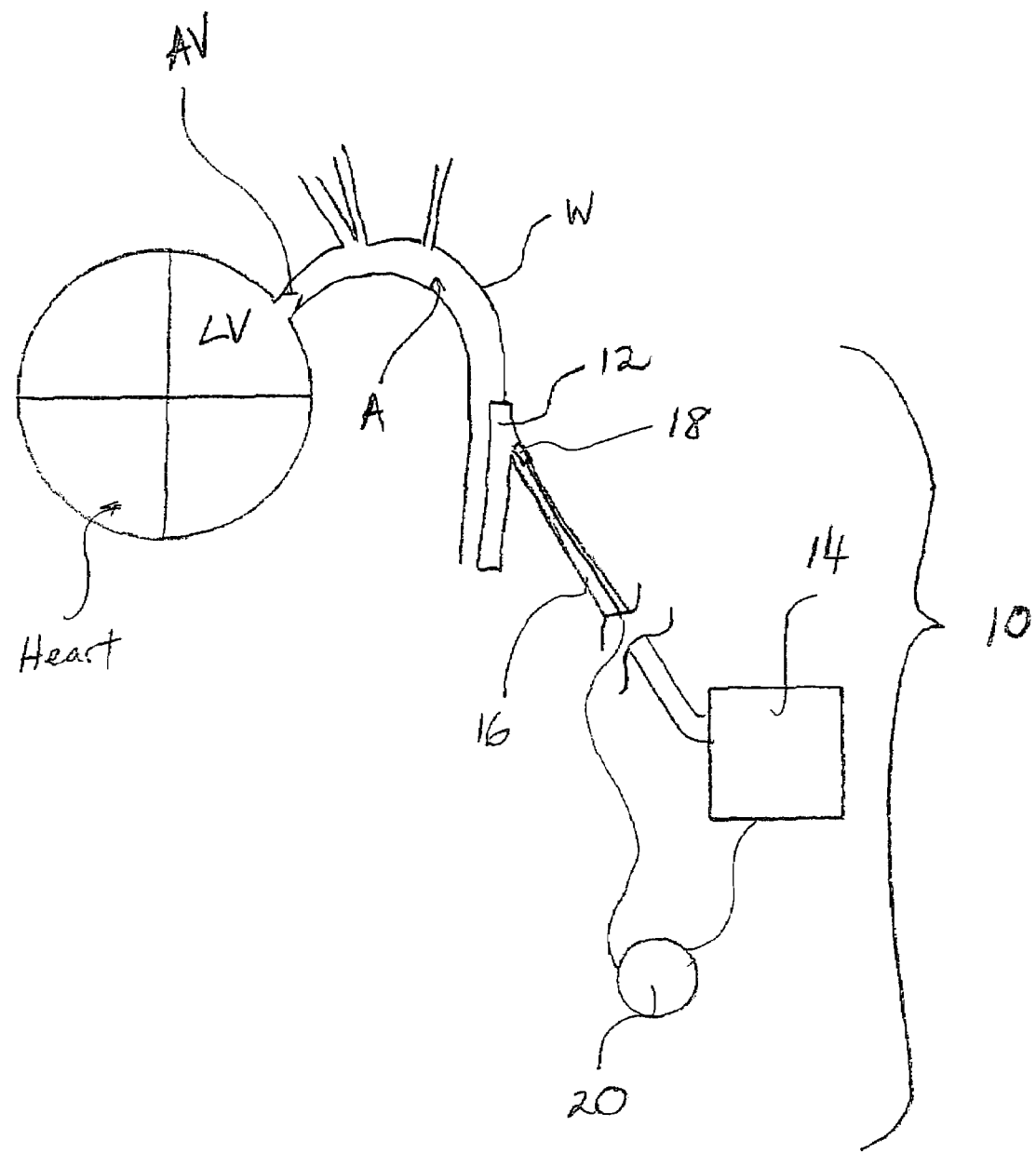
FIG. 1 is a schematic illustrating a typical arrangement of system components according to the present invention.

The present invention has utility as a synchronization system between closure of the aortic valve and a cardiac assist device. The present invention utilizes an acoustic or mechanical force associated with closure of the aortic valve as an input signal for the precise timing of counter-pulsation for an assist device. An inventive system is particularly well suited for endoscopic or minimally invasive insertion of a cardiac assist device.

According to the present invention, an acoustic sensor or mechanical force sensor is placed in proximity to the aortic valve in order to accurately sense aortic valve closure with the use of this signal as a timing input to a cardiac assist device such as an LVAD. The acoustic sensor preferably takes the form of a microphone, ultrasonic transducer or Doppler sensor. More preferably, the acoustic sensor is dimensioned so as to be surgically implantable. Preferably, a mechanical sensor according to the present invention is an accelerometer and more preferably, an accelerometer suitable for implantation. The present invention affords a direct marker of aortic valve closure that is in contrast to the prior art usage of blood pressure as a secondary indicator of this event.

Referring now to FIG. 1, the position of an inventive synchronization system relative to a cardiac system is shown generally at 10 relative to a mammalian left ventricle LV and aorta A. The system 10 is depicted as attached to the aorta A along the descending portion thereof. The system 10 includes an inflatable chamber 12 in fluid communication with a pump 14 by way of a fluid conduit 16. It is appreciated that while the inflatable chamber 12 is depicted as being coupled to a wall W of the aorta A that intra-aortic and cuff-type inflatable chambers are equally as well operative herewith. Additionally, while the inflatable chamber 12 is depicted as being located within the descending portion of the aorta A, placement within an ascending portion of an inflatable chamber within the ascending portion of the aorta A is also operative herewith. The relative location of an inflatable chamber relative to portions of the aorta being within the purview of one skilled in the art and including factors such as chamber size, chamber curvature, chamber elasticity, aorta curvature, and the type of inflatable chamber, as detailed above.

A sensor 18 responsive to acceleration forces or acoustic signatures associated with movement of the aortic valve AV is placed in proximity to the aortic valve AV. Preferably, the sensor 18 is placed within the fluid conduit 16 proximal to the inflatable chamber 12. The fluid conduit 16 transmits fluid between the pump 14 and inflatable chamber 12 to selectably inflate and deflate the chamber 12. Fluids used for this purpose illustratively include air, helium, nitrogen, argon, saline, and combinations thereof. The sensor 18 in this position is able to sense aortic valve AV movement from within the protective environment of the cardiac assist device and as such exhibits superior operating lifetime and offers greater ease of replacement, as compared to a conventional arterial pressure transducer. It is appreciated that the sensor 18 is also readily placed within the inflatable chamber 12 provided that care is taken so as not to damage the inflatable wall of the chamber 12 through contact with the sensor 18. It is further appreciated that other cardiac assist mechanisms are known to the art that are not based on driving a master slave compressor with compressurable fluids, such as myoplasty, electromagnetic cuffs, and an cardiomyoplasty or aortomyoplasty. Cardiomyoplasty and aortomyoplasty are well known to the art as evidenced by Hayward, Heart 1999; 82: 263-264; Salmons et al., Br. Heart J 1992; 68: 333-338; Lee et al., J. Thorac. Cardiovasc. Surg. 1991; 102 (5): 757-765; and Girsch et al., Eur. J. Cardiothorac. Surg. 1998; 13(1): 78-83. The present invention is equally operative herewith. The sensor 18 is a microphone, ultrasonic probe/transducer, Doppler sensor, or a mechanical force accelerometer. An exemplary implantable accelerometer operative herein is detailed in U.S. Pat. Nos. 3,972,038 and 5,674,258.

Force or acoustic transmission delays based on the relative position between the aortic valve AV and the sensor 18 are readily compensated for with an algorithm well understood to the art. Parameters to be considered in a compensating algorithm illustratively include distance between aortic valve and the sensor, orientation of the sensor, transmissivity of blood, transmissivity of pump fluid, and transmissivity of chamber wall material. Preferably, the sensor signal whether collected in digital or analog form is in the form of a digital input signal to the timing controller 20 for the pump 14.

It is appreciated that in addition to monitoring the aortic valve AV closure event, additional events surrounding valve closure are also monitored according to the present invention. For instance, the ejection velocity of blood from the left ventricle LV slows and even reverses direction in some congenital conditions as the pressure on either side of the aortic valve AV equilibrates. A Doppler sensor is recognized to be able to measure velocity changes preceding the actual closure of the aortic valve AV. Further, subsequent to the closure of the aortic valve a back pressure is created thereon associated with the recoil of the aortic wall W. The mechanical systole associated with aortic wall recoil optionally serves as an additional parameter to precisely time the operation of a cardiac assist device by taking into consideration aortic elasticity to calculate with greater accuracy the specific instance of optimal assist device counter pulsation.

A sensor input signal to the pump controller 20 is used in a variety of ways to time chamber counter pulsation. By way of example, the historical timing of aortic valve closure from at least one preceding cardiac cycle is used to time cardiac assist device chamber inflation. Preferably, a windowing algorithm as described in U.S. Pat. No. 4,809,681 is used when historical cardiac cycle data is the signal input for inflatable chamber counter-pulsation. Alternatively, real-time sensor output is used to trigger chamber counter-pulsation for the same cardiac cycle. It is further appreciated that a combination of historical cardiac cycle and real-time cardiac cycle sensing are also operative to trigger assist device counter-pulsation according to the present invention.

In an alternate embodiment, an inventive sensor is surgically attached to the aortic wall. Based on the size of the sensor, it is appreciated that a sensor can be affixed to the aortic wall through endoscopic surgical techniques. The sensor is also readily placed in other locations illustratively including a carotid artery, pericardial wall, subcostally, on an exterior surface of an assist device, and on a pacemaker electrode. An inventive sensor not confined within an LVAD affords the ability to position the sensor for optimal monitoring of aortic valve closure even though such a position is often a less desirable location for the placement of the LVAD. Preferably, a sensor external to an LVAD is a microphone fixed directly to the aortic wall and aimed at the aortic valve from a distance of less than 5 cm. A sensor external to an LVAD is secured in a predetermined position by conventional techniques illustratively including sutures, tissue adhesives, and combinations thereof.

Publications cited herein are indicative of the level of skill in the art to which the invention pertains. Each publication is hereby incorporated by reference to the same extent as if each publication was individually and explicitly incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. A cardiac assist device synchronization system comprising:
   a cardiac assist device coupled to a mammal having a thoracic cavity containing a mammalian heart having an aorta and an aortic valve comprising:
   an inflatable chamber;
   a fluid pump;
   a fluid conduit in fluid communication between said chamber and said pump; and
   a pump controller triggering said pump in counter-pulsation to a mammalian heart; and
   a sensor implanted in the thoracic cavity proximal to the aortic valve;
   said sensor located at a position selected from the group comprising within said fluid conduit, within said inflatable chamber, and exterior to said aorta; and
   said sensor selected from the group consisting of: acoustic and accelerometer, said sensor providing a signal input to said controller indicating closure of the aortic valve.

2. The system of claim 1 wherein said cardiac assist device is a left ventricular assist device.

3. The system of claim 2 wherein said left ventricular assist device is selected from a group consisting of: cuff type, intra-aortic balloon, aortic patch, and aortic conduit.

4. The system of claim 1 wherein said sensor is a microphone.

5. The system of claim 1 wherein said sensor is an ultrasonic transducer and receiver.

6. The system of claim 1 wherein said sensor is a Doppler sensor.

7. The system of claim 1 wherein said sensor is an accelerometer.

8. The system of claim 1 wherein said sensor is located within said fluid conduit.

9. The system of claim 1 wherein said sensor is affixed within the thoracic cavity independent of cardiac assist device components selected from the group consisting of said inflatable chamber and said fluid conduit.

10. The system of claim 1 wherein said sensor is affixed directly to an aortic wail of the aorta proximic to the aortic valve.

11. The system of claim 10 wherein said sensor is affixed with a suture, tissue adhesive or other method of securing said sensor to the aorta.

12. A kit for improving cardiac function comprising: a cardiac assist device synchronization system according to claim 1 along with instructions for the surgical implantation and operation thereof.

* * * * *